United States Patent [19]

Su

[11] Patent Number: 5,270,321
[45] Date of Patent: Dec. 14, 1993

[54] USE OF DICENTRINE AND ITS DERIVATIVES FOR THE TREATMENT OF ARRHYTHMIA

[75] Inventor: Ming-Jai Su, Taipei, Taiwan

[73] Assignee: National Science Council

[21] Appl. No.: 944,235

[22] Filed: Sep. 14, 1992

Related U.S. Application Data

[62] Division of Ser. No. 801,275, Dec. 2, 1991.

[51] Int. Cl.$^5$ .................... A61K 31/44; A61K 31/335
[52] U.S. Cl. .................................. 514/280; 514/463; 514/821
[58] Field of Search ..................... 424/195.1; 514/463, 514/821, 280

[56] References Cited

PUBLICATIONS

Goodman & Gilman "The Pharmacological Basis of Therapeutics" pp. 846–849 and 227 (1987).
C. C. Chen et al., Planta Med. 57:408–410 (1991, Oct.).
Che-Ming Teng et al, Br. J. Pharmacol. 104(3):651–656, Oct (1991).
Kato et al Biological Abst. 76(2) No. 12861 (1982).
Kondo et al Biological Abst. 90(12) No. 137154 (1990).

Primary Examiner—Frederick E. Waddell
Assistant Examiner—Gregory Hook
Attorney, Agent, or Firm—Michael D. Bednarek

[57] ABSTRACT

A method of arrhythmia with an effective amount of dicentrine or other alkaloids extracted from *Lindera oldhammii* (*megaphylla*) Hemsl.

4 Claims, No Drawings

USE OF DICENTRINE AND ITS DERIVATIVES FOR THE TREATMENT OF ARRHYTHMIA

This application is a divisional application of U.S. patent application Ser. No. 07/801,275 filed Dec. 2, 1991 and currently pending.

BACKGROUND OF THE INVENTION

Cardiac arrhythmia is a disorder of rate, rhythm, or conduction of electrical impulses within the heart. They are often associated with coronary artery diseases, e.g. myocardial infarction and atherosclerotic heart disease. Arrhythmia can eventually cause a decrease of mechanical efficiency of the heart, reducing cardiac output. As a result, arrhythmia can have life-threatening effects that require immediate intervention. Many antiarrhythmic drugs act by blocking myocardial $Na^+$ or $Ca^{++}$ ion channels or by prolonging the cardiac action potential duration through the inhibition of potassium currents which are responsible for action potential repolarization.

Lu et al. isolated dicentrine and other alkaloids from the plant *Lindera oldhamii* (megaphylla) Hemsl (Yakugaku Zasshi, 92; 910–917, 1972), but they did not show any biological activity of these compounds.

SUMMARY OF THE INVENTION

It is an object of the present invention to provide an pharmaceutical composition which comprises an effective amount of dicentrine or other alkaloids extracted from *Lindera oldhamii* (megaphylla) Hems1 for the treatment of arrhythmia.

For achieving the above-mentioned object, in a large scale screening test, we found ethylacetate soluble fractions of *Lindera oldhamii* (megaphylla) Hemsl possess platelet inhibition, vasorelaxation and antiarrhythmic action. They inhibited the aggregation of washed rabbit platelets induced by ADP, collagen, arachidonic acid and platelet-activating factor (PAF). They also inhibited norepinephrine-induced contraction of rat thoracic aorta. Furthermore, the action potential of rat ventricular cells was prolonged by these fractions. After re-chromatograph on a silica gel column with n-hexane-ethylacetate (2:1), four potent compounds, dicentrine, N-methylnandigerine, N-methylovigenine and dicentrinone were obtained.

DESCRIPTION OF THE INVENTION

According to the present invention, dicentrine was found to be the most potent vasorelaxant in rat thoracic aorta. It is an $\alpha_1$-adrenoceptor antagonist as revealed by its competitive antagonism of norepinephrine- or phenylephrine-induced vasoconstriction of rat aorta. These effects still persisted in denuded aorta. It did not affect the aortic contraction induced by thromboxane receptor agonist U-46619, angiotensin II, high potassium or carbachol. Contraction of guinea-pig trachea caused by histamine or carbachol was slightly inhibited, while B-adrenoceptor relaxation to isoprenaline in trachea was not affected. In anesthetized rats, i.v. bolus of dicentrine (0.1–1.0 mg/kg) caused a dose-related reduction in mean arterial blood pressure, which reached a maximum within 5 to 10 min after injection and persisted throughout 2 hr observation period. The hypotensive activity of dicentrine was completely abolished after $\alpha_1$-adrenoceptor blockade. In conscious spontaneously hypertensive (SH) and normotensive (NT) rats, dicentrine also evoked dose-related decreases in mean arterial pressure which were of greater magnitude in SH than in NT rats. With oral administration to conscious SH rats, the hypotensive effect persisted over 15 hr. In rats fed with cholesterol-triglyceride-rich diet, the contractile force of aorta increased to twice that of normal diet rats. Dicentrine not only decreased the serum triglyceride level but also restored the contractile force of cholesterol-triglyceride-treated rat aorta back to normal values.

In rat ventricular cells, the effects of dicentrine on action potential and membrane current were studied. At a stimulation frequency of 0.1 Hz, dicentrine prolonged the action potential, increased the time to peak and reduced the initial upstroke amplitude. A voltage clamp study revealed that the prolongation of action potential by dicentrine was associated with a significant inhibition of both transient outward and steady state outward current. However, calcium current was less affected. The inhibition of the upstroke amplitude by dicentrine was correlated with its inhibition of fast sodium inward current. These results indicate that dicentrine may exert antiarrhythmic action.

The active compounds of this invention can be administered by any conventional means available for use in conjunction with pharmaceuticals; either as individual therapeutic active ingredient or in a combination of therapeutic active ingredients. Ordinarily, 1 to 10 mg per day is effective to obtain desired results. The active ingredients can be admixed with pharmaceutically acceptable diluent and carrier, so that it can be administered orally in solid dosage forms, such as capsules, tablets, and powders, or in liquid dosage forms, such as elixirs, syrups, and suspensions, it can also be administered parenterally, in sterile liquid dosage forms.

The following examples serve to demonstrate the pharmacological activities of the claimed compounds. These are not intended as limiting since numerous modifications and varieties wherein will be apparent to those skilled in the art.

EXAMPLE 1

The dried, ground root material (500 g) was extracted with 95% ethanol, and the extract was concentrated in vacua and fractionated into ethanol- and ethylacetate-soluble fractions. The ethylacetate-soluble fraction was then applied to a column of silica gel and eight fractions were obtained. As shown in Table 1, many fractions possessed inhibitory effects on the platelet aggregation induced by arachidonic acid and collagen, and on the vasoconstriction induced by norepinephrine.

From fractions 5–8 rechromatographed on silica gel column, several compounds were further purified. According to their spectral analysis and comparison with the physical constants in the literature (Lu et al., Yakugaku Zasshi 92: 910–917, 1972), four compounds were identified as dicentrine, N-methylnandigerine, N-methylovigerine and dicentrinone.

TABLE 1

| Fraction | Platelet Aggregation (%) | | Aortic Contraction (%) | |
|---|---|---|---|---|
| | Arachidonic acid | Collagen | NE-phasic | NE-tonic |
| Control | 87.6 ± 1.6 | 88.9 ± 1.4 | 100.0 ± 16.8 | 100.0 ± 1.4 |
| 1 | 0.0 ± 0.0*** | 84.1 ± 1.9 | 132.7 ± 12.2 | 96.1 ± 2.7 |
| 2 | spontaneous aggregation | | 130.6 ± 13.7 | 91.8 ± 1.6* |
| 3 | 74.0 ± 2.3*** | 83.5 ± 2.8 | 130.0 ± 21.2 | 94.7 ± 15.5 |
| 4 | 58.2 ± 6.2*** | 79.7 ± 5.0* | 186.6 ± 37.7 | 115.0 ± 14.3 |
| 5 | 0.0 ± 0.0*** | 0.0 ± 0.0** | 25.0 ± 17.7* | 2.1 ± 1.5*** |
| 6 | 0.0 ± 0.0*** | 20.9 ± 8.4*** | 68.9 ± 10.2 | 24.0 ± 4.5*** |
| 7 | 0.0 ± 0.0*** | 0.0 ± 0.0*** | 5.0 ± 3.5** | 1.9 ± 1.3*** |
| 8 | 0.0 ± 0.0*** | 0.0 ± 0.0*** | 0.0 ± 0.0*** | 0.0 ± 0.0*** |

Means ± S.E.M. are presented.
*$P < 0.05$,
**$P < 0.01$,
***$P < 0.001$ as compared with the respective control.
Concentration: arachidonic acid (100 μM), collagen (10 μg/ml), norepinephrine (NE, 3 μM), each fraction (100 μg/ml).

EXAMPLE 2

Concentration-response curve analysis of norepinephrine- and phenylephrine-induced contraction of rat thoracic aortae was performed for the $\alpha_1$-adrenoceptor antagonism by dicentrine in comparison with prazosin, yohimbine and phentolamine. As shown in Table 2, dicentrine was less potent than prazosin, but was much more potent than phentolamine or yohimbine. In all cases the Schild slopes were not significantly different from 1.0.

TABLE 2

| Agonist | Antagonist | pA₂ | slope | r |
|---|---|---|---|---|
| Norepinephrine | Dicentrine | 8.19 ± 0.09 | 0.94 (0.85–1.2) | 0.99 |
| Phenylephrine | Dicentrine | 9.01 ± 0.10 | 0.94 (0.95–1.32) | 0.99 |
| | Prazosin | 10.60 ± 0.10 | 0.95 (0.94–1.24) | 0.99 |
| | Yohimbine | 6.20 ± 0.05 | 0.84 (0.65–1.03) | 0.99 |
| | Phentolamine | 7.53 ± 0.10 | 0.72 (0.70–1.20) | 0.99 |

Results are given as means ± S.E.M. or the mean with 95% confidence limits in parentheses.

Results are given as means±S.E.M. or the mean with 95% confidence limits in parentheses.

EXAMPLE 3

The effects of dicentrine and quinidine on action potential were compared and studied in rat ventricular cells. As shown in Table 3, cells bathed in $Ca^{++}$-Tyrode, 3 to 5 min exposure to 3 μM dicentrine prolonged the action potential duration ($APD_{50}$) from 59.9±11.3 msec to 201.9±28.7 msec. In addition to the prolongation of $APD_{50}$, a depression of initial upstroke amplitude from 138.3±2.6 mV to 125.5±4.5 mV and prolongation of the time to peak amplitude from 5.0±0.5 msec to 10.0±1.9 msec were observed. For cells treated with 3 μM quinidine, similar effects were obtained.

TABLE 3

| | AP amplitude (mV) | $APD_{50}$ (msec) | $T_p$ (msec) |
|---|---|---|---|
| A. Control | 138.3 ± 2.6 | 59.9 ± 11.3 | 5.0 ± 0.5 |
| Dicentrine | 125.5 ± 4.5* | 201.9 ± 28.7* | 10.0 ± 1.9* |
| B. Control | 135.2 ± 2.2 | 62.6 ± 3.9 | 5.3 ± 0.5 |

TABLE 3-continued

| | AP amplitude (mV) | $APD_{50}$ (msec) | $T_p$ (msec) |
|---|---|---|---|
| Quinidine | 121.2 ± 2.3* | 276.0 ± 18.6* | 10.8 ± 2.4* |

Means ± S.E.M. are presented.
*$P < 0.05$ as compared with the respective control.
$APD_{50}$: action potential duration measured at 50% repolarization from the peak amplitude.
$T_p$: time to peak measured from the start of depolarization to the peak of the action potential.
Concentration: dicentrine (3 μM), quinidine (3 μM).

Means±S.E.M. are presented. *: $P<0.05$ as compared with the respective control.
$APD_{50}$: action potential duration measured at 50% repolarization from the peak amplitude.
$T_p$: (25 Tp time to peak measured from the start of depolarization to the peak of the action potential.
Concentration: dicentrine (3 μM), quinidine (3 μM).

EXAMPLE 4

Effects of dicentrine and prasozin or systemic hemodynamic parameters of pentobarbital-anesthetized rats were compared and shown in Table 4. Dicentrine is similar to pyrazosin, another $\alpha_1$-adrenoceptor blocker, both drugs produce similar hemodynamic changes: a decrease in mean arterial pressure (MAP), a reduction in total peripheral resistance by increasing blood flow, little or no change in cardiac output (CO). However, dicentrine produces no change in heart rate (HR), or stroke volume (SV) in comparison with prazosin.

TABLE 4

| Hemodynamic Parameters | Dicentrine (1.0 mg/kg) | | Prazosin (0.1 mg/kg) | |
|---|---|---|---|---|
| | Before | After | Before | After |
| MAP (mm Hg) | 122 ± 5 | 62 ± 5*** | 120 ± 4 | 68 ± 6*** |
| HR (bpm) | 353 ± 10 | 348 ± 8 | 367 ± 9 | 337 ± 10* |
| CO (ml/min) | 21 ± 2 | 25 ± 4 | 27 ± 3 | 32 ± 3 |
| SV (μ/min/beat) | 50 ± 3 | 55 ± 9 | 64 ± 4 | 79 ± 7* |
| Blood flow | 7 ± 4 | 200 ± 27** | 7 ± 4 | 171 ± 14** |

*$P < 0.05$;
**$P < 0.01$,
***$P < 0.001$ before vs. after.

EXAMPLE 5

If rats fed with high cholesterol and high fat diet for three weeks, the maximal contractile force of isolated thoracic aorta increased two folds, as shown in Table 5. If dicentrine was administered orally twice a day (10 mg/kg) in the last week, the maximal contractile force of isolated thoracic aorta was restored to normal range. Prazosin had similar effect at a dose of 5 mg/kg.

TABLE 5

| Treatment | Concentration of phenylephrine (M) | | | | |
|---|---|---|---|---|---|
| | $3 \times 10^{-8}$ | $10^{-7}$ | $3 \times 10^{-7}$ | $10^{-6}$ | $3 \times 10^{-6}$ |
| Normal diet | $0.2 \pm .04^a$ | $.48 \pm .05$ | $0.69 \pm .10$ | $0.86 \pm .15$ | $0.94 \pm .18$ |
| High cholesterol & fat diet | $0.71 \pm .10$ | $1.14 \pm .10$ | $1.55 \pm .10$ | $1.73 \pm .10$ | $1.87 \pm .10$ |
| High cholesterol & fat diet + dicentrine | $0.22 \pm .05$ | $0.55 \pm .07$ | $0.55 \pm .07$ | $0.67 \pm .11$ | $0.75 \pm .12$ |
| High cholesterol & fat diet + prazosin | $0.30 \pm .05$ | $0.51 \pm .08$ | $0.70 \pm .09$ | $0.80 \pm .12$ | $0.87 \pm .12$ |

$^a$contractile force (g); dosage: dicentrine (10 mg/kg), prazosin (5 mg/kg)

What is claimed is:

1. A method for treating arrhythmia in a subject in need thereof, comprising administering to said subject a pharmaceutical composition which comprises an effective amount of dicentrine or a pharmaceutically acceptable salt thereof and a pharmaceutically acceptable carrier.

2. The method of claim 1 wherein the effective amount is administered orally in solid dosage form.

3. The method of claim 1 wherein the effective amount is administered orally in liquid dosage form.

4. The method of claim 1, wherein the effective amount is administered parenterally.

* * * * *